United States Patent
Yukumoto et al.

(10) Patent No.: US 8,721,890 B2
(45) Date of Patent: May 13, 2014

(54) DEHYDRATING SYSTEM AND DEHYDRATING METHOD

(75) Inventors: Atsuhiro Yukumoto, Hiroshima (JP); Hiroyuki Osora, Hiroshima (JP); Yoshio Seiki, Hiroshima (JP); Haruaki Hirayama, Mihara (JP); Kazuto Kobayashi, Hiroshima (JP); Yukio Tanaka, Hiroshima (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 758 days.

(21) Appl. No.: 12/665,854

(22) PCT Filed: Dec. 24, 2008

(86) PCT No.: PCT/JP2008/073373
§ 371 (c)(1),
(2), (4) Date: Dec. 21, 2009

(87) PCT Pub. No.: WO2009/084522
PCT Pub. Date: Jul. 9, 2009

(65) Prior Publication Data
US 2010/0320148 A1 Dec. 23, 2010

(30) Foreign Application Priority Data
Dec. 28, 2007 (JP) .................. 2007-339131

(51) Int. Cl.
*B01D 15/00* (2006.01)
*B01D 35/18* (2006.01)
*C02F 3/12* (2006.01)
*C02F 1/02* (2006.01)
*C02F 1/00* (2006.01)

(52) U.S. Cl.
USPC ............... 210/640; 210/175; 210/195.2; 96/4

(58) Field of Classification Search
USPC ........... 210/640, 195.1, 175, 455, 180; 95/52, 95/47; 96/4; 203/19
See application file for complete search history.

(56) References Cited

U.S. PATENT DOCUMENTS 4,264,338 A * 4/1981 Null .................................. 95/47
4,894,163 A * 1/1990 Watanabe et al. ............. 210/640
(Continued)

FOREIGN PATENT DOCUMENTS

EP 0294827 A2 12/1988
EP 0655274 A1 5/1995
(Continued)

OTHER PUBLICATIONS

International Search Report of PCT/JP2008/073373, mailing date of Feb. 17, 2009.
(Continued)

*Primary Examiner* — Ana Fortuna
(74) *Attorney, Agent, or Firm* — Westerman, Hattori, Daniels & Adrian, LLP

(57) ABSTRACT

A dehydrating system using multiple water separation membranes aims to prevent damage to the water separation membrane units and also to take appropriate measures against decrease in water permeation rate of the water separation membranes. Provided is a dehydrating system (100) for removing water from a target fluid, including at least two water separation membrane units (1, 2, 3) connected in series in a flow direction of the target fluid; two or more heat exchangers (11, 21, 31) respectively provided in front of the water separation membrane units (1, 2, 3), each of the heat exchangers (11, 21, 31) raising a temperature of the target fluid to a temperature which is lower than a boiling point of the target fluid but close to the boiling point.

12 Claims, 4 Drawing Sheets

(56) References Cited

U.S. PATENT DOCUMENTS

| | | | | |
|---|---|---|---|---|
| 4,895,989 | A | * | 1/1990 | Sander et al. ............... 568/851 |
| 4,962,270 | A | | 10/1990 | Feimer et al. |
| 5,192,445 | A | * | 3/1993 | Bartels ........................ 210/640 |
| 5,266,206 | A | * | 11/1993 | Baker et al. ................. 210/640 |
| 5,464,540 | A | * | 11/1995 | Friesen et al. ............... 210/640 |
| 5,681,433 | A | * | 10/1997 | Friesen et al. ................. 203/39 |
| 8,128,826 | B2 | * | 3/2012 | Plante et al. ................. 210/640 |
| 2003/0233934 | A1 | | 12/2003 | Wijmans et al. |
| 2004/0004040 | A1 | * | 1/2004 | Colling et al. .............. 210/641 |
| 2008/0099400 | A1 | * | 5/2008 | Nemser et al. .............. 210/638 |
| 2009/0057224 | A1 | * | 3/2009 | Huang et al. ................ 210/640 |

FOREIGN PATENT DOCUMENTS

| | | |
|---|---|---|
| EP | 0835860 A1 | 4/1998 |
| JP | 58-95523 A | 6/1983 |
| JP | 58-128107 A | 7/1983 |
| JP | 4-22423 A | 1/1992 |
| JP | 7-124444 A | 5/1995 |

OTHER PUBLICATIONS

Extended European Search Report dated Nov. 5, 2013, issued in corresponding European Patent Application No. 08868848.6.

* cited by examiner

FIG.4(a)    FIG.4(b)    FIG.4(c)
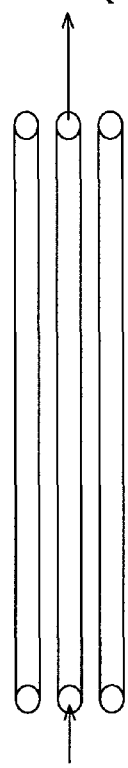
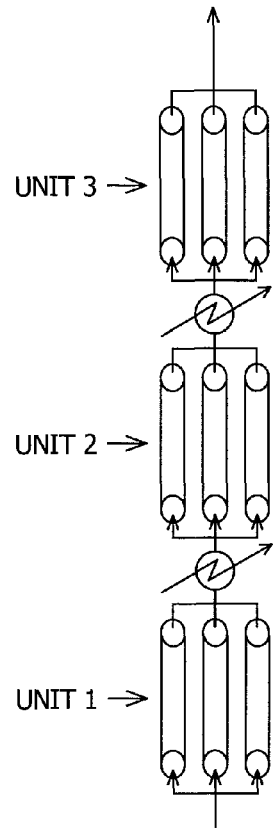
UNIT 3
UNIT 2
UNIT 1
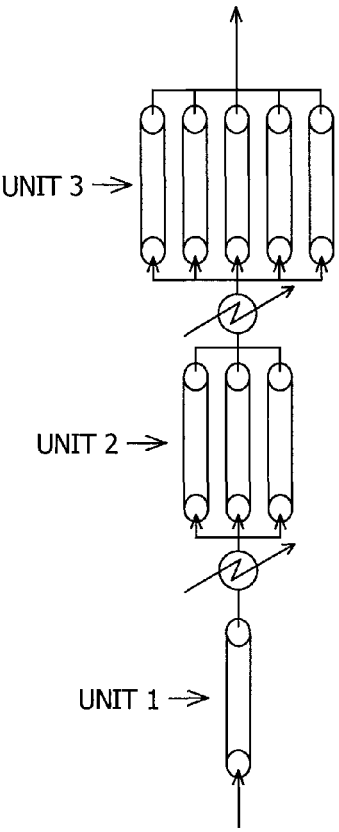
UNIT 3
UNIT 2
UNIT 1
FIG.5
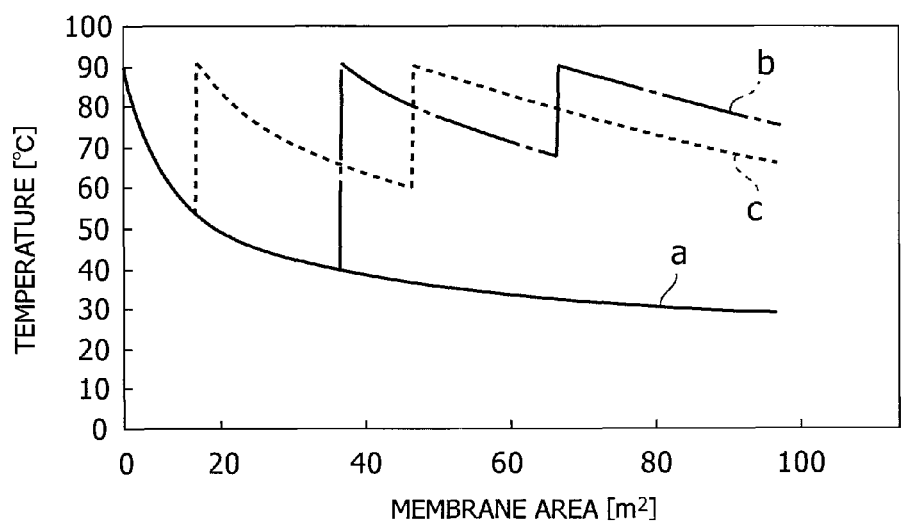

DEHYDRATING SYSTEM AND DEHYDRATING METHOD

TECHNICAL FIELD

The present invention relates to a dehydrating system and to a dehydrating method which use water separation membranes. More specifically, the present invention relates to a dehydrating system and to a dehydrating method in which damage to the water separation membranes is prevented in dehydrating a mixture (target fluid) of water with one of ethanol and propanol, each of which forms an azeotropic composition with water. Moreover, the dehydrating system and the dehydrating method of the present invention take appropriate measures against decrease in permeation rate of water, which is the separation target.

BACKGROUND ART

Ethanol has attracted attention as a fuel source alternative to petroleum fuels. The market scale of ethanol is estimated to be 55 million kiloliters for 2010. However, to adopt ethanol as a fuel, it is necessary to concentrate roughly distilled crude ethanol obtained from biomass such as corn to at least 99.5 wt % by dehydration.

One method for the dehydration is a pervaporation method using a water separation membrane as shown in FIG. 6(a). The pervaporation method refers to a method in which a target component such as water, for example, is removed in a gas state from a target fluid by using a membrane. In the pervaporation method, the temperature of a target fluid such as 95% roughly distilled ethanol is raised in a heat exchanger 61, and then the target fluid is fed to a feed side 62. The pressure on a permeation side 63, which is the other side of a water separation membrane, is reduced, creating a chemical potential difference produced across two sides of the water separation membrane 64. By this chemical potential difference, it is possible to cause the target component such as water, for example, to permeate from the feed side 62 to the permeation side 63. As a result, the pervaporation method makes it possible to remove, in a gas state, the target component such as water, for example, from the target fluid. Note that in FIG. 6(a), the reference numeral (65) denotes a condenser for condensing a permeate through the membrane, and the reference numeral (66) denotes a vacuum pump.

However, in the pervaporation method, if a water separation membrane with a high permeation rate of water, which is the separation target, is used, the evaporation of the permeated component significantly lowers the temperature of the target fluid. Therefore, in a case in which a water separation membrane with a high water permeation rate is used, the temperature of the target fluid on the feed side 62 significantly decreases as the target fluid goes from an inlet side A to an outlet side B as shown in FIG. 6b. In general, decrease in temperature of the target fluid significantly lowers the water permeation rate of a water separation membrane. When water separation membrane units are connected in series in the flow direction of a non-treated fluid, the temperature of the target fluid further decreases in the second water separation membrane unit, thereby significantly lowering the water permeation rates of the water separation membranes in and after the second water separation membrane unit.

In this connection, there has been proposed a use of a component not involving the above drawbacks (Patent Literature 1: Japanese Unexamined Patent Application Publication No. Hei 7-124444). Patent Literature 1 discloses a pervaporation membrane separation system in which at least one gas-liquid two-phase flow generating unit is provided upstream of pervaporation membrane separation units. This pervaporation membrane separation system includes multiple membrane separation units connected in series. In the pervaporation membrane separation system, a heat exchanger for maintaining the temperature of a raw material liquid is provided upstream of the first membrane separation unit to which the raw material is first fed.

However, when a non-treated fluid flows into a membrane unit as a gas-liquid two-phase flow, droplets of the non-treated fluid repeatedly collide with the surface of the membrane, thereby producing a problem of causing mechanical damage.

Moreover, it has been known that the boiling point of a target fluid decreases in a water separation membrane unit. This decrease in boiling point of a target fluid is probably caused by change in concentration of ethanol, pressure drop, or the like. The present inventors assumed that the boiling point of a target fluid is decreased by pressure drop.

Here, when the temperature of a target fluid exceeds the boiling point thereof, cavitation erosion occurs in the water separation membrane unit. The cavitation erosion refers to a phenomenon in which repeated events of generation and collapse of small bubbles due to local boiling phenomena damage materials by a high impact pressure generated when the bubbles collapse. For this reason, to prevent the water separation membrane units from being damaged, the target temperatures of the target fluid in the heat exchangers need to be set lower for further downstream water separation membrane units.

[Patent Literature 1] Japanese Unexamined Patent Application Publication No. Hei 7-124444

DISCLOSURE OF THE INVENTION

Problems to be Solved by the Invention

The present invention has been made in view of the above circumstances. An object of the present invention is to provide a dehydrating system and a dehydrating method for a plant provided with multiple water separation membrane units, in which damage to the water separation membrane units is prevented by setting target temperatures of a target fluid lower for further downstream water separation membrane units.

In addition, another object of the present invention is to provide a dehydrating system and a dehydrating method for a plant provided with multiple water separation membrane units, which are capable of maintaining high water permeabilities of water separation membranes in the water separation membrane units by raising the temperature of the target fluid to a temperature which is lower than a boiling point of the target fluid but close to the boiling point by use of a heat exchanger.

Means for Solving the Problems

To achieve the above objects, the present invention provides a dehydrating system for removing water from a target fluid, including: at least two water separation membrane units connected in series in a flow direction of the target fluid; and two or more heat exchangers respectively provided in front of the water separation membrane units, each of the heat exchangers raising a temperature of the target fluid to a temperature which is lower than a boiling point thereof but close to the boiling point.

In the dehydrating system according to the present invention, each of the temperatures of the target fluid lower than a boiling point is preferably a temperature lower than the corresponding boiling point of the target fluid by 5° C., in consideration of occurrence of error in measuring the temperature of the non-treated fluid due to occurrence of distribution in temperature and concentration of the non-treated fluid.

Moreover, in consideration of human error at the setting of the temperature raise for the heat exchangers, in all dehydrating systems according to the present invention, each of the temperatures lower than the corresponding boiling point of the target fluid is preferably a temperature which is lower, by 5° C., than the boiling point of the target fluid at an outlet of the last water separation membrane unit of the at least two water separation membrane units.

Preferably, in one embodiment of the dehydrating system according to the present invention, all the water separation membrane units have an identical membrane area.

Preferably, in another embodiment of the dehydrating system according to the present invention, the water separation membrane units have such mutually different membrane areas that the membrane areas of the water separation membrane units become larger in the flow direction of the target fluid.

In the dehydrating system according to the present invention, the target fluid is generally an organic aqueous solution. Preferably, an organic component of the organic aqueous solution is one organic component selected from the group consisting of alcohols such as ethanol, propanol, isopropanol, and glycols, carboxylic acids such as acetic acid, ethers such as dimethyl ether and diethyl ether, aldehydes such as acetaldehyde, ketones such as acetone and methyl ethyl ketone, and esters such as ethyl acetate, and is soluble in water.

In one embodiment, the dehydrating system according to the present invention includes thermometers for monitoring temperatures of the target fluid as monitoring devices, and the thermometers are respectively provided to the water separation membrane units.

In another embodiment, the dehydrating system according to the present invention includes concentration meters for monitoring concentrations of the target fluid as monitoring devices, and the concentration meters are respectively provided to the water separation membrane units.

The dehydrating method of the present invention is a method of dehydrating a target fluid, using a dehydrating system including: at least two water separation membrane units connected in series in a flow direction of the target fluid; and two or more heat exchangers respectively provided in front of the water separation membrane units, each of the heat exchangers raising a temperature of the target fluid. Preferably, the dehydrating method includes the steps of: causing each of the heat exchangers to raise a temperature of the target fluid to a temperature which is lower than a boiling point of the target fluid but close to the boiling point; and causing each of the water separation membrane units to remove water from the target fluid.

In the dehydrating method according to the present invention, each of the temperatures of the target fluid lower than a boiling point is preferably a temperature lower than the corresponding boiling point of the target fluid by 5° C., in consideration of occurrence of error in measuring the temperature of the non-treated fluid due to occurrence of distribution in temperature and concentration of the non-treated fluid.

In the dehydrating method according to the present invention, in consideration of human error in the setting of the temperature rise for the heat exchangers, each of the temperatures lower than the corresponding boiling point of the target fluid is preferably a temperature which is lower, by 5° C., than the boiling point of the target fluid at an outlet of the last water separation membrane unit of the at least two water separation membrane units.

Preferably, in one embodiment of the dehydrating method according to the present invention, water separation membrane units having an identical membrane area are respectively used as the water separation membrane units.

Preferably, in another embodiment of the dehydrating method according to the present invention, as the water separation membrane units, water separation membrane units are used which have such mutually different membrane areas that the membrane areas of the water separation membrane units become larger in the flow direction of the target fluid.

In the dehydrating method according to the present invention, the target fluid is generally an organic aqueous solution. Preferably, an organic component of the organic aqueous solution is one organic component selected from the group consisting of alcohols such as ethanol, propanol, isopropanol, and glycols, carboxylic acids such as acetic acid, ethers such as dimethyl ether and diethyl ether, aldehydes such as acetaldehyde, ketones such as acetone and methyl ethyl ketone, and esters such as ethyl acetate, and is soluble in water.

In one embodiment of the dehydrating method according to the present invention, thermometers for monitoring temperatures of the target fluid are used as monitoring devices, and water separation membrane units provided with the thermometers are used as the water separation membrane units, respectively.

In another embodiment of the dehydrating system according to the present invention, concentration meters for monitoring concentrations of the target fluid are used as monitoring devices, and water separation membrane units provided with the concentration meters are used as the water separation membrane units, respectively.

Effects of the Invention

The present invention provides a dehydrating system and a dehydrating method capable of preventing cavitation erosion due to pressure drop of the target fluid from occurring in water separation membrane units by an appropriate temperature control achieved by using heat exchangers.

In addition, the present invention makes it possible to provide a dehydrating system and a dehydrating method for a plant provided with multiple water separation membrane units, which are capable of maintaining high water permeabilities of water separation membranes in the water separation membrane units by raising the temperature of the target fluid to a temperature which is lower than a boiling point of the target fluid but close to the boiling point.

BRIEF DESCRIPTION OF DRAWINGS

FIG. 4 is a conceptual diagram for describing the forms of water separation membranes in Example 1.

FIG. 5 is a graph showing change in temperature against membrane area in Example 1.

EXPLANATION OF REFERENCE NUMERALS

Figure 1:
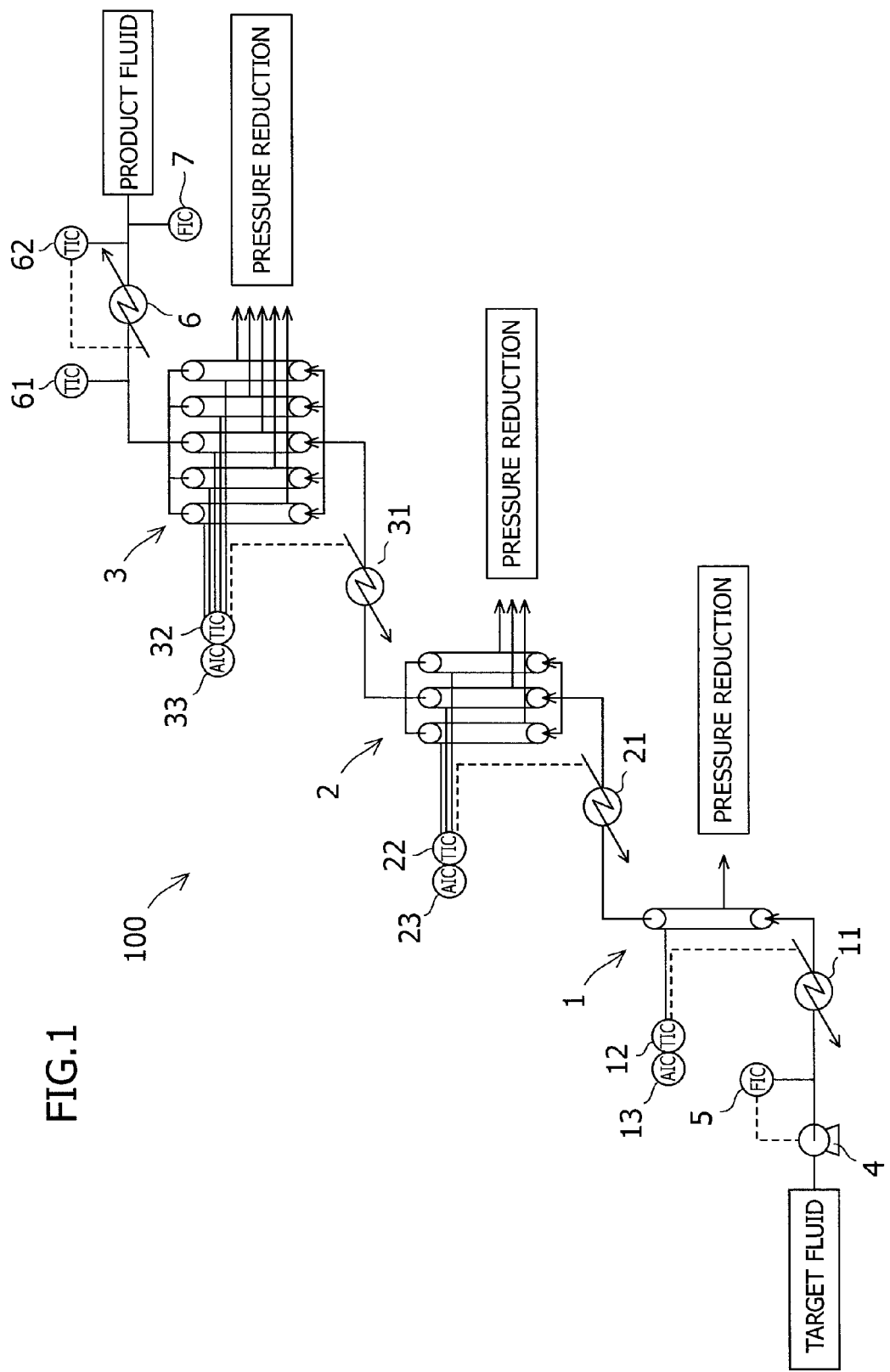
FIG. 1 is a conceptual diagram for describing an embodiment of a dehydrating system according to the present invention.

1 Water separation membrane unit
2 Water separation membrane unit
3 Water separation membrane unit
4 Pump
5 Inlet flow meter
6 Condenser
7 Outlet flow meter
11 Heat exchanger
12 Thermometer
13 Concentration meter
21 Heat exchanger
22 Thermometer
23 Concentration meter
31 Heat exchanger
32 Thermometer
33 Concentration meter
61 Thermometer
62 Thermometer
100 Dehydrating system

BEST MODES FOR CARRYING OUT THE INVENTION

Hereinafter, a dehydrating system according to the present invention will be described in further detail with reference to embodiments thereof. FIG. 1 shows an embodiment of the dehydrating system according to the present invention.

FIG. 1 is a drawing showing the embodiment of the dehydrating system according to the present invention. A dehydrating system 100 according to this embodiment includes, as main components, water separation membrane units (1, 2, and 3), heat exchangers (11, 21, and 31), thermometers (12, 22, 32, 61, and 62), concentration meters (13, 23, and 33), a pump 4, an inlet flow meter 5, a condenser 6 and an outlet flow meter 7.

In this embodiment, the water separation membrane unit 2 is designed to have three times the membrane area of the water separation membrane unit 1. Moreover, the water separation membrane unit 3 is designed to have five times the membrane area of the water separation membrane unit 1. In other words, as shown in FIG. 1, the water separation membrane unit 1 includes one water separation membrane, the water separation membrane unit 2 includes three water separation membranes, and the water separation membrane unit 3 includes five water separation membranes.

For example, when the target fluid is crude ethanol, the water separation membrane units 1 to 3 are units for separating the crude ethanol into absolute ethanol and water. Silica-based or zeolite-based inorganic water separation membranes with pore diameters of 10 angstroms or less are suitable as water separation membranes for constructing the water separation membrane units.

An inorganic water separation membrane described in Japanese Patent No. 2808479 may also be used. The inorganic water separation membrane according to Japanese Patent No. 2808479 is an acid-resistant composite water separation membrane obtained by supporting, in pores of a porous inorganic material, silica gel obtained through hydrolysis of an ethoxy or methoxy group-containing alkoxysilane. The acid-resistant composite water separation membrane can be produced by a production method including the following Steps 1 to 11.

Note that, as a porous base member to be described below, a base member of a ceramic such as alumina, silica, zirconia, or titania is usually used, and preferable is a cylindrical base member having multiple inner tubes which extend in the longitudinal direction, each of which having a circular cross-section. In the following Steps 1 to 11, the inorganic water separation membrane is formed in a way that the inorganic water separation membrane covers inner walls of such inner tubes. The phrase "supporting, in pores of a porous inorganic material, silica gel obtained through hydrolysis of an ethoxy or methoxy group-containing alkoxysilane" means this state.

Besides the inorganic water separation membrane, an organic membrane such as a polyvinyl alcohol membrane, a polyimide membrane or a polyamide membrane can be used as a membrane main body of the water separation membrane formed in the water separation membrane.

Step 1: Blending ratios of raw materials for silica sols to be supported in preparation conditions for multiple kinds of silica sols produced by changing the mixing ratio of an alkoxysilane, which is a raw material of silica sols, water, and an acid catalyst are divided into two kinds, that is, for a silica sol 1 and for a silica sol 2.

Step 2: The weight ratio of water to an alkoxysilane for the raw material of the silica sol 1 is set to 0.5 to 2.0, and the weight ratio of an acid catalyst, which is a reaction catalyst, to the alkoxysilane is set to 0.01 to 0.1.

Step 3: The weight ratio of water to an alkoxysilane for the raw material of the silica sol 2 is set to 2.0 to 50, and the weight ratio of an acid catalyst, which is a reaction catalyst, to the alkoxysilane is set to 0.01 to 0.5.

Step 4: While the above-mentioned raw materials for the silica sol 1 are kept boiling, a liquid approximately 25 minutes after, a liquid approximately 20 minutes after, and a liquid approximately 15 minutes after the start of the boiling are taken as 1-A, 1-B and 1-C liquids, respectively.

Step 5: The above-mentioned raw materials for the silica gel 2 are stirred and mixed at room temperature for 30 minutes to 90 minutes, to produce the silica sol 2.

Step 6: The silica sol 1-A liquid is supported on a surface of a porous base member. Then, the porous base member is baked for 5 to 15 minutes in an electric furnace set at approximately 200° C. Next, the porous base member is baked for 5 to 15 minutes in an electric furnace set at approximately 300° C. Subsequently, the porous base member is baked for 5 to 15 minutes in an electric furnace set at approximately 400° C. Thereafter, the porous base member is baked for 5 to 15 minutes in an electric furnace set at approximately 500° C.

Step 7: The silica sol 1-A liquid is further supported on the surface of the porous base member on which the silica sol 1-A liquid has been supported. Thereafter, the operation in Step 6 is repeated two to three times.

Step 8: Next, by using the silica sol 1-B liquid, similar treatment as in Step 6 and Step 7 is further performed on the surface of the porous base member on which the silica sol 1-A liquid has been supported.

Step 9: Next, by using the silica sol 1-C liquid, similar treatment as in Step 6 and Step 7 is performed on the surface of the porous base member on which the silica sol 1-B liquid has been supported.

Step 10: Next, the silica sol 2 liquid is supported on the surface of the porous base member on which the silica sol 1-A, 1-B and 1-C liquids have been supported. Then, the porous base member is baked for 5 to 15 minutes in an electric furnace set at approximately 200° C. Next, the porous member is baked for 5 to 15 minutes in an electric furnace set at approximately 300° C. Subsequently, the porous base member is baked for 5 to 15 minutes in an electric furnace set at approximately 400° C. Thereafter, the porous base member is baked for 5 to 15 minutes in an electric furnace set at approximately 500° C.

Step 11: The silica sol 2 liquid is further supported on the surface of the porous base member on which the silica sol 2 liquid has been supported. Thereafter, the operation in Step 10 is repeated two or three times.

Via Steps 1 to 11 described above, the inorganic water separation membrane can be produced. In the present invention, such inorganic water separation membranes are used as the water separation membranes housed in the water separation membrane units 1 to 3, for example. In the water separation membrane units, such cylindrical water separation membranes are housed in containers whose inside pressure can be reduced.

The pump 4 causes the target fluid to pass through the inlet flow meter 5, the thermometer 12, and the heat exchanger 11 and to be introduced into the water separation membrane unit 1. The target fluid flows in inner tubes of the cylindrical water separation membrane, i.e., flows on the feed side. Here, the temperature of the target fluid is previously raised in the heat exchanger 11. Here, the temperature of the target fluid is set to a temperature which is lower than a boiling point, but close to the boiling point This is because, if the temperature of the target fluid exceeds the boiling point thereof, cavitation occurs in the water separation membrane unit, thereby damaging the water separation membrane.

Relative to the pressure on the feed side, the pressure on the permeation side, i.e., the other side, of the water separation membrane is reduced in the water separation membrane. Hence, a chemical potential difference across two sides of the water separation membrane (membrane main body) is created. Thereby, a target component in the target fluid is separated from the feed side to the permeation side. Here, as the target component evaporates, the temperature of the target fluid decreases.

Subsequently, the target fluid passes through the concentration meter 13 and the thermometer 22, and it is reheated in the heat exchanger 21. Here, the boiling point of the target fluid is lowered because of pressure drop in the water separation membrane unit 1. Accordingly, the heat exchanger 21 raises the temperature of the target fluid to a temperature which is lower than the temperature set in the heat exchanger 11.

Next, the target fluid is introduced into the water separation membrane unit 2, where the target component is separated therefrom in a similar manner. The target fluid passes through the concentration meter 23 and the thermometer 32, and heated again in the heat exchanger 31. The boiling point of the target fluid is further lowered in the water separation membrane unit 2. Thus, the temperature set in the heat exchanger 31 is further lowered than the temperature set in the heat exchanger 21. Subsequently, the target fluid is introduced to the water separation membrane unit 3, where the target component is separated from the target fluid in a similar manner.

The target fluid passes through the concentration meter 33 and the thermometer 61, and is cooled to room temperature in the condenser 6. Subsequently, the target fluid passes through the outlet flow meter 7, and is taken out as product fluid. In this embodiment of the dehydrating system according to the present invention, the water separation membrane unit 2 is designed to have three times the membrane area of the water separation membrane unit 1. Furthermore, the water separation membrane unit 3 is designed to have five times the membrane area of the water separation membrane unit 1. As described above, in this embodiment, the separation membrane units have mutually different membrane areas which are larger downstream than upstream of the flow of the target fluid. This makes it possible to prevent the temperature of the target fluid from sharply decreasing in the water separation membrane unit 1, thereby maintaining the temperature of the target fluid at high levels in the water separation membrane units 1 to 3. Accordingly, by employing the configuration of this embodiment, the permeabilities of the water separation membranes throughout the dehydrating system can be improved, and thereby high-quality product fluid can be taken out.

If the conditions permit, the dehydrating system according to the present invention may have water separation membrane units having an identical membrane area. Also, in this form, damage to the water separation membranes can be prevented by raising the temperature of the target fluid to a temperature which is lower than the boiling point of the target fluid but close to the boiling point. Moreover, also in this form, the permeabilities of the water separation membranes throughout the dehydrating system can be improved.

In the dehydrating system according to the present invention, the target fluid is an organic aqueous solution, and preferably one organic component selected from the group consisting of alcohols such as ethanol, propanol, isopropanol, and glycols, carboxylic acids such as acetic acid, ethers such as dimethyl ether and diethyl ether, aldehydes such as acetaldehyde, ketones such as acetone and methyl ethyl ketone, and esters such as ethyl acetate.

Next, description is made of a first mode of a method of removing water from crude ethanol by using the dehydrating system according to this embodiment.

The method according to the first mode is designed for a case in which the target fluid to be dehydrated is crude ethanol. As for concentration, this crude ethanol aqueous solution is assumed to be an approximately 90 to 95 wt % ethanol aqueous solution. Specifically, crude ethanol containing ethanol as the organic component is the target fluid. The ethanol concentration of an eventually obtained product fluid, i.e., product ethanol (absolute ethanol) is 99.5 wt % to 99.8 wt %.

Being pressurized with the pump 4, the crude ethanol passes through the inlet flow meter 5, the thermometer 12 and the heat exchanger 11, and is introduced into the water separation membrane unit 1. Here, the temperature of the crude ethanol is raised in the heat exchanger 11, and reaches 90° C. At this time, the temperature of the crude ethanol is set lower than the boiling point of the crude ethanol by 5° C. This is because, if the temperature of the crude ethanol exceeds the boiling point thereof cavitation erosion occurs in the water separation membrane unit, thereby damaging the water separation membrane.

Figure 2:
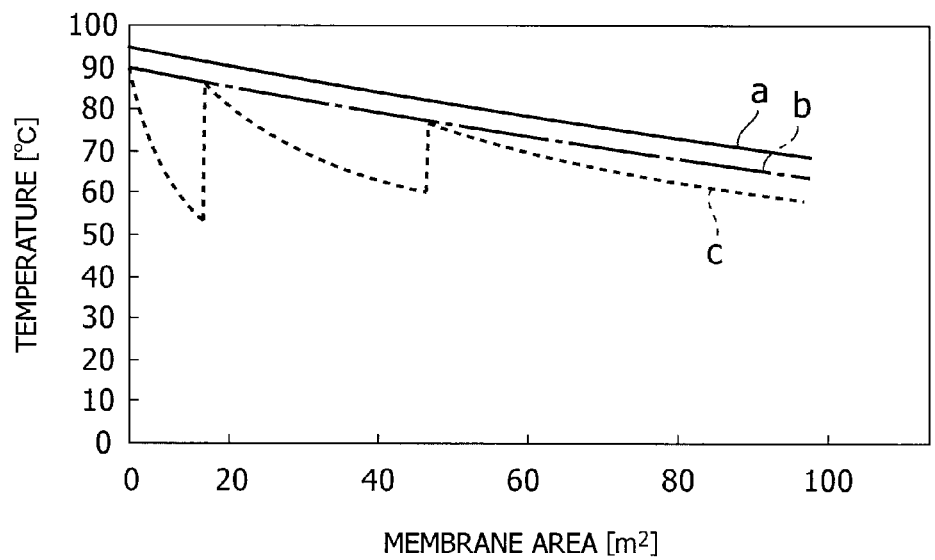
FIG. 2 is a graph showing change in temperature against membrane area in a method according to a first mode in which the dehydrating system according to the present invention is used.

FIG. 2 shows change in temperature against membrane area in the first mode of the dehydrating system according to the present invention. In FIG. 2, lines a, b and c represent change in boiling point of the crude ethanol, change in temperature set as the target, and change in temperature of the crude ethanol (target fluid), respectively.

The temperature of the crude ethanol (target fluid) after passing through the water separation membrane unit 1 decreases to approximately 55° C. because of water evaporation. The crude ethanol (target fluid) passes through the concentration meter 13 and the thermometer 22, and it is reheated in the heat exchanger 21. Here, as shown in FIG. 2, the boiling point of the crude ethanol has decreased to 92° C. because of pressure drop in the water separation membrane unit 1.

Accordingly, to prevent cavitation erosion from occurring in the water separation membrane unit 2, the temperature of the crude ethanol is set to 87° C., which is lower than the boiling point temperature thereof by 5° C.

Subsequently, the crude ethanol (target fluid) is introduced into the water separation membrane unit 2, where water is separated therefrom. The temperature of the crude ethanol decreases to approximately 60° C. The crude ethanol (target fluid) is reheated in the heat exchanger 31. Here, the boiling point of the crude ethanol (target fluid) has further decreased to 83° C. Accordingly, the heat exchanger 31 raises the temperature of the crude ethanol to 78° C. Next, the crude ethanol (target fluid) is introduced into the water separation membrane unit 3, where the temperature of the crude ethanol (target fluid) decreases to approximately 68 degrees.

Next, the temperature of the crude ethanol (target fluid) is decreased to room temperature in the condenser 6. The crude ethanol (target fluid) passes through the outlet flow meter 7, and is taken out as product ethanol.

As described above, in the method according to the first mode, through the appropriate temperature control by the heat exchangers, the dehydrating system 100 is capable of preventing the cavitation erosion from occurring in the water separation membrane units, thereby allowing the system to be operated without damage to the water separation membranes.

Next, description will be made of a second mode of the method of removing water from crude ethanol by using the dehydrating system according to this embodiment.

In the second mode, each of the heat exchangers 11, 21, and 31 raises the temperature of the crude ethanol to 70° C. This temperature set as the target is determined on the basis of the boiling point of the crude ethanol at an outlet of the last unit of the multiple water separation membrane units connected in series. Here, the water separation membrane unit 3 corresponds to the last unit. Specifically, the temperature of the crude ethanol is raised to a temperature which is lower, by 5° C., than the boiling point of the crude ethanol at the outlet of the water separation membrane unit 3. This makes it possible to avoid human error at the setting of temperature rise for the heat exchangers, thereby surely avoiding damage to the membranes due to the cavitation erosion.

The second mode is also designed for a case in which the target fluid to be dehydrated is an approximately 90 to 95 wt % crude ethanol aqueous solution. Similarly, the ethanol concentration of the eventually obtained product fluid, i.e., product ethanol (absolute ethanol) is 99.5 wt % to 99.8 wt %.

The pump 4 causes the crude ethanol to pass through the inlet flow meter 5, the thermometer 12 and the heat exchanger 11, and to be introduced into the water separation membrane unit 1. Here, the crude ethanol is preheated in the heat exchanger 11 to 70° C.

Figure 3:
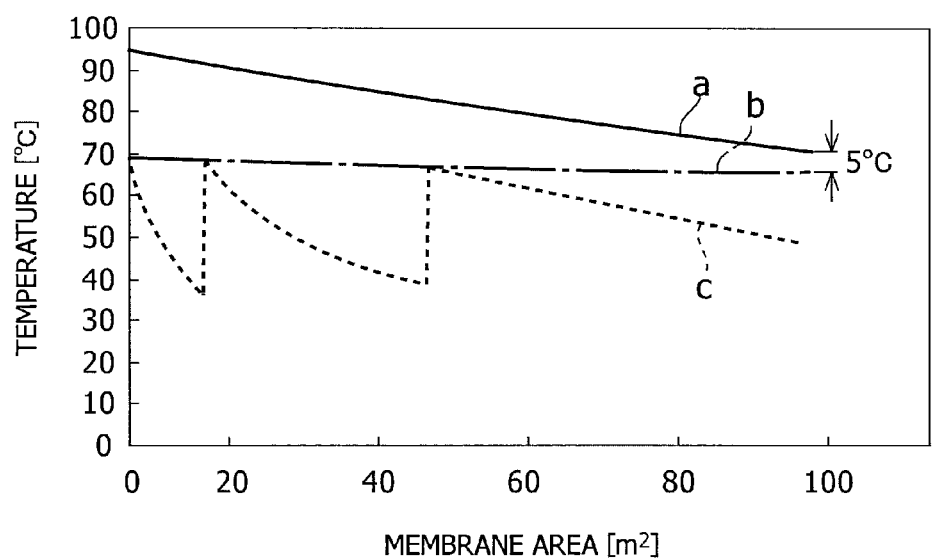
FIG. 3 is a graph showing change in temperature against membrane area in a method according to a second mode in which the dehydrating system according to the present invention is used.
Figure 6A:
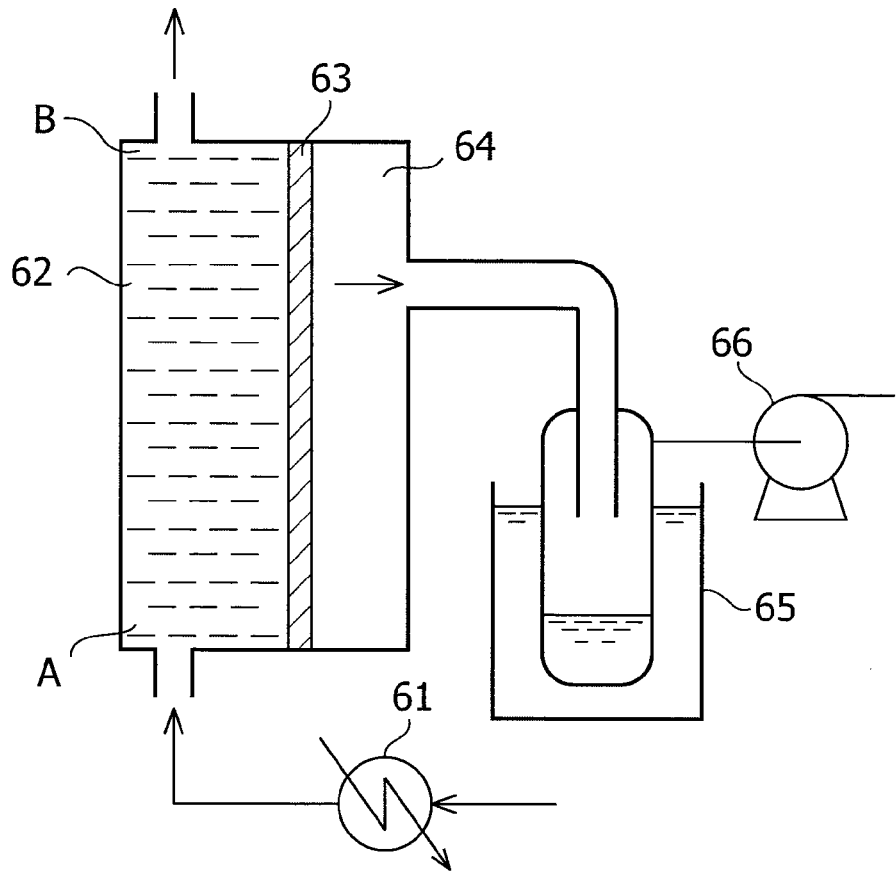
FIG. 6(a) is a conceptual diagram for describing a pervaporation method using a water separation membrane
Figure 6B:
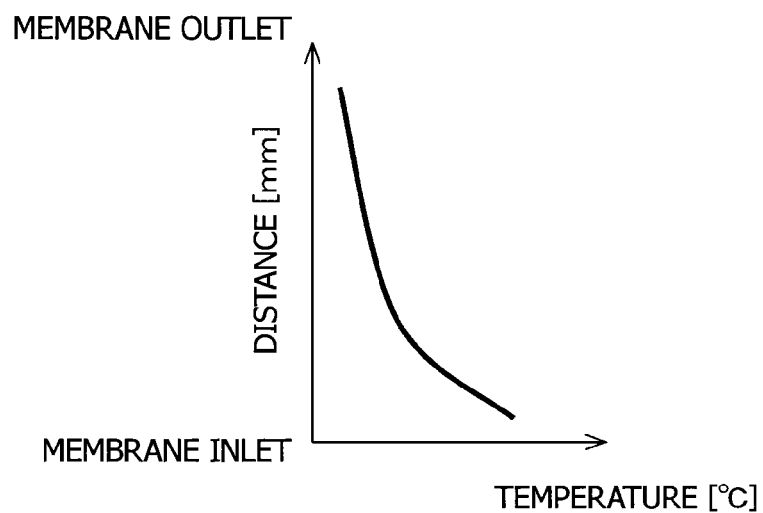
FIG. 6(b) is a graph showing change in water separation membrane temperature of a cylindrical water separation membrane.

FIG. 3 shows change in temperature against membrane area in the second mode of the dehydrating system according to the present invention. In FIG. 3, lines a, b and c represent change in boiling point of the crude ethanol, change in temperature set as the target, and change in temperature of the crude ethanol (target fluid), respectively.

The temperature of the crude ethanol after passing through the water separation membrane unit 1 decreases to approximately 37° C. because of water evaporation. The crude ethanol passes through the thermometer 12, and it is reheated in the heat exchanger 21. Here, as shown in FIG. 3, the boiling point of the crude ethanol has decreased to 92° C. because of pressure drop in the water separation membrane unit 1. Here, the heat exchanger 21 heats the crude ethanol to 70° C.

Next, the crude ethanol is introduced into the water separation membrane unit 2. The temperature of the crude ethanol decreases to approximately 40° C. because of the water separation. The crude ethanol is reheated in the heat exchanger 31. Here, the boiling point of the crude ethanol has further decreased to 83° C. The heat exchanger 31 heats the crude ethanol to 70° C. Subsequently, the crude ethanol is introduced into the water separation membrane unit 3, where the temperature of the crude ethanol is decreased to approximately 50° C.

The temperature of the crude ethanol decreases to room temperature in the condenser 6. The crude ethanol passes through the outlet flow meter 7, and is taken out as product ethanol. As described above, the second mode makes it possible to further lower the possibility of occurrence of the cavitation erosion, as compared to the system described in the first mode. Accordingly, the second mode provides a dehydrating system which is safer to operate than the system described in the first mode.

Note that, in each of the method according to the first mode and the method according to the second mode, used are the water separation membrane unit 1 having one water separation membrane, the water separation membrane unit 2 having three water separation membranes, and the water separation membrane unit 3 having five water separation membranes. However, the numbers of the water separation membranes in the water separation membrane units can be set as appropriate in accordance with conditions in the first mode or the second mode. In other word, the numbers of the water separation membranes in the water separation membrane units may be the same.

Example 1

FIG. 4 shows the forms of water separation membranes in Example 1. Water separation membrane units 1 to 3 are connected. In a dehydrating system (Case a), no heat exchangers are provided between the water separation membrane units. In another dehydrating system (Case b), the membrane areas of the water separation membrane units 1 to 3 are the same. In still another dehydrating system (Case c), the membrane area of the water separation membrane unit 2 is three times the membrane area of the water separation membrane unit 1, and the membrane area of the water separation membrane unit 3 is five times that of the membrane area of the water separation membrane unit 1. For each Case, dehydration was performed on 95 wt % crude ethanol. Note that, in Case c, the dehydrating system 100 described in FIG. 1 was used. The total areas of the membranes in respective Cases are the same (100 m$^2$).

FIG. 5 shows changes in temperature against membrane area in Example 1. In Case a, the temperature of the crude ethanol decreased to 30° C. at a membrane area of 100 m$^2$. Meanwhile, in Cases b and c, even at a membrane area of 100 m$^2$, the temperatures remained at about 70 to 80° C. The configurations in which heat exchangers are provided between the water separation membrane units were able to maintain the permeabilities of the water separation membranes at higher levels.

Comparison of Case b and Case c shows that the temperature is maintained at a higher level in Case c from the fact that the lowest temperature in Case b is 40° C. and the lowest temperature in Case c is 50° C. Lastly, the final concentrations in Cases a to c were 97.6%, 99.2%, and 99.5%, respectively.

The invention claimed is:
1. A dehydrating system for removing water from a target fluid, comprising:
at least two water separation membrane units connected in series in a flow direction of the target fluid; and two or more heat exchangers respectively provided in front of the water separation membrane units, each of the heat exchangers raising a temperature of the target fluid to a temperature which is lower than a boiling point thereof but close to the boiling point, wherein the water separation membrane units have membrane areas of increasing size in the flow direction of the target fluid, wherein water separation membranes in the units are silica- or zeolite-based, inorganic water separation membrane with pore diameters of 10 angstroms or less.

2. The dehydrating system according to claim 1, wherein the temperature of the target fluid lower than the boiling point is a temperature which is lower than the boiling point of the target fluid by 5° C.

3. The dehydrating system according to claim 1, wherein the temperature of the target fluid lower than the boiling point is a temperature lower than, by 5° C., a boiling point of the target fluid at an outlet of the last water separation membrane unit of the at least two water separation membrane units.

4. The dehydrating system according to claim 1, wherein the target fluid is an organic aqueous solution.

5. The dehydrating system according to claim 4, wherein an organic component of the organic aqueous solution is one organic component selected from the group consisting of alcohols such as ethanol, propanol, isopropanol, and glycols, carboxylic acids such as acetic acid, ethers such as dimethyl ether and diethyl ether, aldehydes such as acetaldehyde, ketones such as acetone and methyl ethyl ketone, and esters such as ethyl acetate, and is soluble in water.

6. The dehydrating system according to claim 1, comprising thermometers for monitoring temperatures of the target fluid as monitoring devices, wherein
the thermometers are respectively provided to the water separation membrane units, and
in the heat exchanger upstream of each water separation membrane, a degree of temperature rise of the target fluid is controlled by using a controller, or is set by monitoring personnel.

7. The dehydrating system according to claim 1, comprising concentration meters for monitoring concentrations of the target fluid as monitoring devices, wherein
the concentration meters are respectively provided to the water separation membrane units, and
in the heat exchanger upstream of each water separation membrane, a degree of temperature rise of the target fluid is controlled by using a controller, or is set by monitoring personnel.

8. A method of dehydrating a target fluid, using a dehydrating system including: at least two water separation membrane units connected in series in a flow direction of the target fluid; and two or more heat exchangers respectively provided in front of the water separation membrane units, each of the heat exchangers raising a temperature of the target fluid, the dehydrating method comprising the steps of:
causing each of the heat exchangers to raise a temperature of the target fluid to a temperature which is lower than a boiling point of the target fluid by 5° C. or a temperature lower than, by 5° C., a boiling point of the target fluid at an outlet of the last water separation membrane unit of the at least two water separation membrane units;
causing each of the water separation membrane units to remove water from the target fluid;
wherein water separation membrane units having mutually different membrane areas are respectively used, and the membrane areas become larger in the fluid direction of the target fluid, and
the water separation membranes in the units are silica- or zeolite-based inorganic water separation membranes with pore diameters of 10 angstroms or less.

9. The dehydrating method according to claim 8, wherein the target fluid is an organic aqueous solution.

10. The dehydrating method according to claim 9, wherein an organic component of the organic aqueous solution is one organic component selected from the group consisting of alcohols such as ethanol, propanol, isopropanol, and glycols, carboxylic acids such as acetic acid, ethers such as dimethyl ether and diethyl ether, aldehydes such as acetaldehyde, ketones such as acetone and methyl ethyl ketone, and esters such as ethyl acetate, and is soluble in water.

11. The dehydrating method according to claim 8, wherein thermometers for monitoring temperatures of the target fluid are used as monitoring devices,
water separation membrane units provided with the thermometers are used as the water separation membrane units, respectively, and
in the heat exchanger upstream of each water separation membrane, a degree of temperature rise of the target fluid is controlled by using a controller, or is set by monitoring personnel.

12. The dehydrating method according to claim 8, wherein concentration meters for monitoring concentrations of the target fluid are used as monitoring devices,
water separation membrane units provided with the concentration meters are used as the water separation membrane units, respectively, and
in the heat exchangers upstream of each water separation membrane, a degree of temperature rise of the target fluid is controlled by using a controller, or is set by monitoring personnel.

* * * * *